US009689001B2

(12) United States Patent
Simpson et al.

(10) Patent No.: US 9,689,001 B2
(45) Date of Patent: Jun. 27, 2017

(54) NOV MINI-PROMOTERS (71) Applicant: The University of British Columbia, Vancouver (CA)

(72) Inventors: Elizabeth M. Simpson, Vancouver (CA); Charles de Leeuw, Seattle, WA (US); Daniel Goldowitz, Port Moody (CA); Wyeth W. Wasserman, Vancouver (CA)

(73) Assignee: UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 15/160,613

(22) Filed: May 20, 2016

(65) Prior Publication Data

US 2016/0340690 A1    Nov. 24, 2016

Related U.S. Application Data (60) Provisional application No. 62/164,679, filed on May 21, 2015.

(51) Int. Cl.
*C12N 15/85*   (2006.01)

(52) U.S. Cl.
CPC ........ *C12N 15/85* (2013.01); *C12N 2830/008* (2013.01)

(58) Field of Classification Search
None
See application file for complete search history.

*Primary Examiner* — Antonio Galisteo Gonzalez
(74) *Attorney, Agent, or Firm* — Pamela J. Sherwood; Bozicevic, Field & Francis LLP (57) ABSTRACT Isolated polynucleotides comprising a NOV mini-promoter are provided. The mini-promoter may be operably linked to an expressible sequence, including, but not limited to, reporter genes, genes encoding a polypeptide of interest, and regulatory RNA sequences such as miRNA, siRNA, and anti-sense RNA. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, including, but not limited to, for identifying or labeling cells, monitoring or tracking the expression of cells and gene therapy.

15 Claims, 2 Drawing Sheets
(2 of 2 Drawing Sheet(s) Filed in Color)

Ple303-icre (NOV RRs) in ssAAV9 virus vEMS46

SEQUENCE LISTING

<160> NUMBER OF SEQ ID NOS: 8

<210> SEQ ID NO 1
<211> LENGTH: 3087
<212> TYPE: DNA
<213> ORGANISM: Homo sapiens

<400> SEQUENCE: 1

```
gcttgagtta tgtatcttag aatatggttt aacaaaagct aaaacctaaa aaaaaaaaag      60
ggcatggcat ccttggtatt tgtgggtgaa ctctgtggtg actgctttaa ttaatttatg     120
taattggaat tcaccaaga cataaattta ctcatatcta tttttaaaga caggaatatt     180
gatcttggac cagcaataaa ttcctgtaat atttgtcctc agtaaaaagc caagacaatt     240
ctaggccatt tctttttgtc ttgaaaacgt tatgccaaaa tcatcatttt gttggctgca     300
tacatcctga tttatattcg atgagagtta taaaaggctt ttatagtgga gatggccgag     360
tgacattttc ctataaatca cgatcatttt tactgctaca aagttctagg actgaacttc     420
aaatacaacc gtgctgtaaa ctctgtggat ggaaccacat acttgctgaa tgagaaacat     480
gtttcccttt caccatgagt gactgcatat tccagtcagt ctctggcaga tgagagcatc     540
actaaaaccc agggaaccat gctcagcttt gatgaagcag cttgtgaaac gcaggtcacc     600
cagaacacct ttgaatacag ctatgctttc agcctcatga ataattcagg tccatataga     660
tgggtgaact ctgtggtgac tgctttaatt aatttatgta attggaattt caccaagaca     720
taaatttact catatctatt tttaaagaca ggaatattga tcttggacca gcaataaatt     780
cctgtaatat ttgtcctcag taaaaagcca agacaattct aggccatttc tttttgtctt     840
gaaaacgtta tgccaaaatc atcattttgt tggctgcata catcctgatt tatattcgat     900
gagagttata aaaggctttt atagtggaga tggccgagtg acattttcct ataaatcacg     960
atcattttta ctgctacaaa gttctaggac tgaacttcaa atacaaccgt gctgtaaact    1020
ctgtggatgg aaccacatac ttgctgaatg agaaacatgt ttcccttca ccatgagtga    1080 ctgcatattc cagtcagtct ctggcagatg agagcatcac taaaacccag ggaaccatgc    1140
tcagctttga tgaagcagct tgtgaaacgc aggtcagaag aacttaccat cttgggaaag    1200
tgataaagct ggatggtctc taacatttac ctaaacttga attggctatt ttttgtacat    1260 acatttttcca tttcaactat tagcttagaa gtttacaaaa gaacagtcca gttttttttt    1320
ttctattata acagatacag cattaccatt tgtaatcgtt gatcaaggca taagcaattt    1380
cttgcttgtc aatttgaaca tctagccagg aataaatagc acacagtatg tgtaatgcaa    1440
tcttcaaagc gttttattgg aacagttctt agacctcata caaggaaata aaaaaataag    1500
aaatgtaaat gaatgtgatg tcagactgag gaagcaagtc tctagagatc cctggaagtt    1560
agaatggatt ttaaaattca ttatgattga attataaaat aaatgaaaac cagcagggtt    1620
aaatatgagg ttgatgggag caagaaaaga aagttatttg atacccatg gcagggagca    1680 tgcaagttca ggttcacctc tagggcaagg aagaattttc ttcaaggttc ttctctttca    1740
gtgtttactc tgtagcaggc actgtgactg tgtaagtggc acacccttaa gatgccccca    1800
agttactttg cccgccttgg tggcccccat ttggtcaccg ggctcactgc gtcttctgtc    1860
ccagctgagt ggtttctcct tgtctcgcct gccttcagtg ttaatttcca gaaaattga    1920 aagaggaggg gttaagttaa acatacactg tgagttgttc ttacgctaca gttgaagaga    1980
gatcttgaaa tatattttc attcattttc tctctttgtg tctcccctat gtgagaaata    2040
tggcatgcac aattggcgcc tatattatcc tctagccaat actttatccc agttgcctta    2100
```

```
gcaactgtca atatttgtct ggtatgtcac agccccagtt ggctgatggc tggttgaaca    2160
tctacttgta aagtttagga aagagagaca cccagtggtc taaattaact gagttgctga    2220
aagcctgctt cattttattt tcacttcaga aatgttatt aattttaaa tctgatcttc      2280 tgttaatcat caacaatccc cacaattaaa cttatgaagg gagaaaagaa catgtgttgg    2340
cacacttact ttttctgtaa agtcccagac agtaaatatt ttaggctttg cggtccccct    2400
gccactcccc tcccccaac acacacacac ttttctcttt ctcctctttc tctccttttcc   2460 tcccttgctt ctctcccctc cctctcaaca cattcaatga gtgccctaaa cggtgacaaa    2520
cttgcatgtg cttccctcat gactaaaccc ctgggccttc tgccaatccc ctgcagatgg    2580
ccccaaactg caggcatccc gtaaggggac cccacgcttg cagccctggt tggaacggtc    2640
agggtggagg aggatggtgg ggagtggtgg tgtcttcgtc ctgggagaag gcgaagcaac    2700
ttccaggagg aaacgggcgt ttccttccca cgcgctcgag cgagccctgg gtcctggcct    2760
cggaactcca cccagcccct ccccaccctc tgggaaaagc cagtcgccac acacaggcac    2820
acgcaggccc cggcgccgcg ccctaaggag agcagcaccc acagccaatt gccatggcaa    2880
ccccggggtt cgttccactt ccccacccag ccgatctccc ccctcctccc tgcactgcag    2940
ccaaccggct gtgcgcgtc ccaggagcgc gctataaaac ctgtgctggg cgtgatcggc     3000
aagcaccgga ccaggggaa ggcgagcagt gccaatctac agcgaagaaa gtctcgtttg    3060
gtaaaagcga gagggaaag cctgagc                                          3087

<210> SEQ ID NO 2
<211> LENGTH: 2426
<212> TYPE: DNA
<213> ORGANISM: Homo sapiens

<400> SEQUENCE: 2
gggtgaactc tgtggtgact gctttaatta atttatgtaa ttggaatttc accaagacat      60
aaatttactc atatctattt ttaaagacag gaatattgat cttggaccag caataaattc     120
ctgtaatatt tgtcctcagt aaaaagccaa gacaattcta ggccatttct ttttgtcttg    180
aaaacgttat gccaaaatca tcattttgtt ggctgcatac atcctgattt atattcgatg    240
agagttataa aaggctttta tagtggagat ggccgagtga cattttccta taaatcacga    300
tcatttttac tgctacaaag ttctaggact gaacttcaaa tacaaccgtg ctgtaaactc    360
tgtggatgga accacatact tgctgaatga gaaacatgtt tccctttcac catgagtgac    420
tgcatattcc agtcagtctc tggcagatga gagcatcact aaaacccagg gaaccatgct    480
cagctttgat gaagcagctt gtgaaacgca ggtcagaaga acttaccatc ttgggaaagt    540
gataaagctg gatggtctct aacatttacc taaacttgaa ttggctattt tttgtacata    600
cattttccat ttcaactatt agcttagaag tttacaaaag aacagtccag ttttttttt    660 tctattataa cagatacagc attaccattt gtaatcgttg atcaaggcat aagcaatttc    720
ttgcttgtca atttgaacat ctagccagga ataaatagca cacagtatgt gtaatgcaat    780
cttcaaagcg ttttattgga acagttctta gacctcatac aaggaaataa aaaaataaga    840
aatgtaaatg aatgtgatgt cagactgagg aagcaagtct ctagagatcc ctggaagtta    900
gaatggattt taaaattcat tatgattgaa ttataaaata aatgaaaacc agcagggtta    960
aatatgaggt tgatgggagc aagaaaagaa agttatttgg ataccatgg cagggagcat    1020 gcaagttcag gttcacctct agggcaagga agaattttct tcaaggttct tctctttcag    1080
tgtttactct gtagcaggca ctgtgactgt gtaagtggca caccctaag atgccccaa      1140
```

```
gttactttgc cgccttggt ggcccccatt tggtcaccgg gctcactgcg tcttctgtcc      1200
cagctgagtg gtttctcctt gtctcgcctg ccttcagtgt taatttccag aaaaattgaa      1260
agaggagggg ttaagttaaa catacactgt gagttgttct tacgctacag ttgaagagag      1320
atcttgaaat atattttca ttcattttct ctctttgtgt ctcccctatg tgagaaatat      1380
ggcatgcaca attggcgcct atattatcct ctagccaata cttatccca gttgccttag      1440 caactgtcaa tatttgtctg gtatgtcaca gccccagttg gctgatggct ggttgaacat      1500
ctacttgtaa agtttaggaa agagagacac ccagtggtct aaattaactg agttgctgaa      1560
agcctgcttc atttattt cacttcagaa atgtttatta atttttaaat ctgatcttct       1620
gttaatcatc aacaatcccc acaattaaac ttatgaaggg agaaaagaac atgtgttggc      1680
acacttactt tttctgtaaa gtcccagaca gtaaatattt taggctttgc ggtcccctg       1740 ccactcccct ccccccaaca cacacacact tttctctttc tcctctttct ctcctttcct      1800
cccttgcttc tctcccctcc ctctcaacac attcaatgag tgccctaaac ggtgacaaac      1860
ttgcatgtgc ttccctcatg actaaacccc tgggccttct gccaatcccc tgcagatggc      1920
cccaaactgc aggcatcccg taaggggacc ccacgcttgc agccctggtt ggaacggtca      1980
gggtggagga ggatggtggg gagtggtggt gtcttcgtcc tgggagaagg cgaagcaact      2040
tccaggagga aacgggcgtt ccttcccac gcgctcgagc gagccctggg tcctggcctc      2100
ggaactccac ccagcccctc ccaccctct gggaaaagcc agtcgccaca cacaggcaca      2160
cgcaggcccc ggcgccgcgc cctaaggaga gcagcaccca cagccaattg ccatggcaac      2220
cccggggttc gttccacttc cccacccagc cgatctcccc cctcctccct gcactgcagc      2280
caaccggctt gtgcgcgtcc caggagcgcg ctataaaacc tgtgctgggc gtgatcggca      2340
agcaccggac caggggaag gcgagcagtg ccaatctaca gcgaagaaag tctcgtttgg      2400
taaaagcgag aggggaaagc ctgagc                                          2426
```

<210> SEQ ID NO 3
<211> LENGTH: 694
<212> TYPE: DNA
<213> ORGANISM: Homo sapiens

<400> SEQUENCE: 3

```
tcccctgcc actcccctcc ccccaacaca cacacacttt tctctttctc ctctttctct        60
cctttcctcc cttgcttctc tcccctccct ctcaacacat tcaatgagtg ccctaaacgg      120
tgacaaactt gcatgtgctt ccctcatgac taaacccctg ggccttctgc caatcccctg      180
cagatggccc caaactgcag gcatcccgta aggggacccc acgcttgcag ccctggttgg      240
aacggtcagg gtgaggagg atggtgggga gtggtggtgt cttcgtcctg ggagaaggcg      300
aagcaacttc caggaggaaa cgggcgtttc cttcccacgc gctcgagcga gccctgggtc      360
ctggcctcgg aactccaccc agcccctccc caccctctgg gaaaagccag tcgccacaca      420
caggcacacg caggccccgg cgccgcgccc taaggagagc agcacccaca gccaattgcc      480
atggcaaccc cggggttcgt tccacttccc cacccagccg atctccccc tcctcctgc       540 actgcagcca accggcttgt gcgcgtccca ggagcgcgct ataaaacctg tgctgggcgt      600
gatcggcaag caccggacca gggggaaggc gagcagtgcc aatctacagc gaagaaagtc      660
tcgtttggta aaagcgagag gggaaagcct gagc                                  694
```

```
<210> SEQ ID NO 4
<211> LENGTH: 661
<212> TYPE: DNA
<213> ORGANISM: Homo sapiens

<400> SEQUENCE: 4
gcttgagtta tgtatcttag aatatggttt aacaaaagct aaaacctaaa aaaaaaaag      60 ggcatggcat ccttggtatt tgtgggtgaa ctctgtggtg actgctttaa ttaatttatg    120
taattggaat tcaccaaga cataaattta ctcatatcta tttttaaaga caggaatatt    180
gatcttggac cagcaataaa ttcctgtaat atttgtcctc agtaaaaagc caagacaatt    240
ctaggccatt tcttttgtc ttgaaaacgt tatgccaaaa tcatcatttt gttggctgca    300
tacatcctga tttatattcg atgagagtta taaaaggctt ttatagtgga gatggccgag    360
tgacattttc ctataaatca cgatcatttt tactgctaca aagttctagg actgaacttc    420
aaatacaacc gtgctgtaaa ctctgtggat ggaaccacat acttgctgaa tgagaaacat    480 gtttccctt caccatgagt gactgcatat tccagtcagt ctctggcaga tgagagcatc    540
actaaaaccc agggaaccat gctcagcttt gatgaagcag cttgtgaaac gcaggtcacc    600
cagaacacct ttgaatacag ctatgctttc agcctcatga ataattcagg tccatataga    660
t                                                                    661

<210> SEQ ID NO 5
<211> LENGTH: 513
<212> TYPE: DNA
<213> ORGANISM: Homo sapiens

<400> SEQUENCE: 5
gggtgaactc tgtggtgact gctttaatta atttatgtaa ttggaatttc accaagacat     60
aaatttactc atatctattt ttaaagacag gaatattgat cttggaccag caataaattc    120
ctgtaatatt tgtcctcagt aaaaagccaa gacaattcta ggccatttct ttttgtcttg    180
aaaacgttat gccaaaatca tcattttgtt ggctgcatac atcctgattt atattcgatg    240
agagttataa aaggctttta tagtggagat ggccgagtga cattttccta taaatcacga    300
tcatttttac tgctacaaag ttctaggact gaacttcaaa tacaaccgtg ctgtaaactc    360
tgtggatgga accacatact tgctgaatga aaacatgtt tccctttcac catgagtgac    420
tgcatattcc agtcagtctc tggcagatga gagcatcact aaaacccagg gaaccatgct    480
cagctttgat gaagcagctt gtgaaacgca ggt                                 513

<210> SEQ ID NO 6
<211> LENGTH: 598
<212> TYPE: DNA
<213> ORGANISM: Homo sapiens

<400> SEQUENCE: 6
cagaagaact taccatcttg ggaaagtgat aaagctggat ggtctctaac atttacctaa     60
acttgaattg gctatttttt gtacatacat tttccatttc aactattagc ttagaagttt    120 acaaagaac agtccagttt ttttttttct attataacag atacagcatt accatttgta    180
atcgttgatc aaggcataag caatttcttg cttgtcaatt tgaacatcta gccaggaata    240
aatagcacac agtatgtgta atgcaatctt caaagcgttt tattggaaca gttcttagac    300
ctcatacaag gaaataaaaa aataagaaat gtaaatgaat gtgatgtcag actgaggaag    360
caagtctcta gagatccctg gaagttagaa tggatttaa aattcattat gattgaatta    420
```

```
taaaataaat gaaaaccagc agggttaaat atgaggttga tgggagcaag aaaagaaagt      480
tatttggata cccatggcag ggagcatgca agttcaggtt cacctctagg gcaaggaaga      540
attttcttca aggttcttct ctttcagtgt ttactctgta gcaggcactg tgactgtg       598

<210> SEQ ID NO 7
<211> LENGTH: 126
<212> TYPE: DNA
<213> ORGANISM: Homo sapiens

<400> SEQUENCE: 7
taagtggcac acccttaaga tgcccccaag ttactttgcc cgccttggtg gcccccattt       60
ggtcaccggg ctcactgcgt cttctgtccc agctgagtgg tttctccttg tctcgcctgc      120
cttcag                                                                126

<210> SEQ ID NO 8
<211> LENGTH: 495
<212> TYPE: DNA
<213> ORGANISM: Homo sapiens

<400> SEQUENCE: 8
tgttaatttc cagaaaaatt gaaagaggag gggttaagtt aaacatacac tgtgagttgt       60
tcttacgcta cagttgaaga gagatcttga aatatatttt tcattcattt tctctctttg      120
tgtctcccct atgtgagaaa tatggcatgc acaattggcg cctatattat cctctagcca      180
atactttatc ccagttgcct tagcaactgt caatatttgt ctggtatgtc acagccccag      240
ttggctgatg gctggttgaa catctacttg taaagtttag gaaagagaga cacccagtgg      300
tctaaattaa ctgagttgct gaaagcctgc ttcattttat tttcacttca gaaatgttta      360 ttaatttta aatctgatct tctgttaatc atcaacaatc cccacaatta aacttatgaa       420
gggagaaaag aacatgtgtt ggcacactta cttttctgt aaagtcccag acagtaaata      480
ttttaggctt tgcgg                                                      495
```

NOV MINI-PROMOTERS

FIELD OF THE INVENTION

The invention relates to gene promoters and regulatory elements. More specifically, the invention relates to novel NOV promoter compositions and related methods.

BACKGROUND

The NOV gene, also known as CCN3, encodes a secreted, extracellular matrix (ECM) associated signaling protein. This biological function implicates NOV as an important gene in cell adhesion, migration, proliferation, differentiation, and survival. The expression pattern on the Allen Brain Atlas data indicates that this gene is in the superficial, midlevel and deep cortex, piriform cortex and hippocampal CA1 and in the basal and lateral nuclei of amygdala. In select sagittal sections, the continuum between hippocampal CA1 region into amygdaloid-hippocampal region and posteriomedial cortical amygdala is shown, and olfactory nuclei/bulb. Endogenous NOV expression has been observed in the adult rat cerebral cortex and amygdala (Su et al. 2001).

There is a need for characterized human NOV promoters for gene expression, for instance in human gene therapy applications. It is in particular useful to identify small promoter elements that are sufficient to drive expression in certain cell types, for instance retinal cells or neurons in the brain. Such small promoter elements, or "mini-promoters" are particularly useful in certain applications, for instance they are more amenable to insertion into viral vectors used in gene therapy applications.

SUMMARY OF THE INVENTION

The present invention provides novel nucleic acid sequence compositions and methods relating to minimal human NOV promoters. The invention is based in part on the surprising discovery that certain minimal NOV promoter elements are capable of expressing in specific cell types, for instance in cells of the brain or eye.

In one embodiment of the invention, there is provided an isolated nucleic acid fragment comprising an NOV mini-promoter, wherein the NOV mini-promoter comprises one or more NOV regulatory elements operably linked in a non-native conformation to a NOV basal promoter. The NOV mini-promoter may have a nucleic acid sequence which is substantially similar in sequence and function to SEQ ID NO: 1 or 2. The NOV basal promoter may have a nucleic acid sequence which is substantially similar in sequence and function to SEQ ID NO: 3. The NOV regulatory element may have a nucleic acid sequence which is substantially similar in sequence and function to one or more of SEQ ID NO: 4-8, e.g. comprising one, two, three, four or five of the regulatory elements set forth in the provided sequences. The NOV mini-promoters may further be operably linked to an expressible sequence, including, but not limited to, reporter genes, genes encoding a polypeptide of interest, and regulatory RNA sequences such as miRNA, siRNA and anti-sense RNA. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin, and the like. The expressible sequence may encode an RNA interference molecule.

In one embodiment, there is provided an expression vector comprising an NOV mini-promoter, wherein the NOV mini-promoter comprises one or more NOV regulatory elements operably linked in a non-native conformation to an NOV basal promoter. The NOV mini-promoter may have a nucleic acid sequence which is substantially similar in sequence and function to SEQ ID NO: 1 or 2. The NOV basal promoter may have a nucleic acid sequence which is substantially similar in sequence and function to SEQ ID NO: 3. The one or more NOV regulatory elements may have a nucleic acid sequence which is substantially similar in sequence and function to SEQ ID NO: 4-8. The NOV mini-promoter may further be operably linked to an expressible sequence including, but not limited to, reporter genes, genes encoding a polypeptide of interest, and regulatory RNA sequences such as miRNA, siRNA, and anti-sense RNA. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell an expression vector comprising an NOV mini-promoter element, wherein the NOV mini-promoter element comprises one or more NOV regulatory elements operably linked in a non-native conformation to an NOV basal promoter element. Cells of interest include cells of the peripheral or central nervous system and progenitors thereof, including, but not limited to embryonic stem cells, neural stem cells, neurons, glial cells, astrocytes, microgial cells; and/or cells in the eye and progenitors thereof, including but not limited to, retinal cells, corneal cells, horizontal cells, Müller glia cells. The NOV mini-promoter may have a nucleic acid sequence which is substantially similar in sequence and function to SEQ ID NO: 1 or 2. The NOV basal promoter may have a nucleic acid sequence which is substantially similar in sequence and function to SEQ ID NO: 3. The NOV regulatory element may have a nucleic acid sequence which is substantially similar in sequence and function to one or more of SEQ ID NO: 4-8. The NOV mini-promoter may further be operably linked to an expressible sequence, including, but not limited to, reporter genes, genes encoding a polypeptide of interest, and regulatory RNA sequences such as miRNA, siRNA, and anti-sense RNA. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising an NOV mini-promoter element, wherein the NOV mini-promoter element comprises one or more NOV regulatory element operably linked in a non-native conformation to a NOV basal promoter element, and wherein the expressible sequence comprises a reporter gene. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to one or more of SEQ ID NO: 4-8. In some embodiments, the cell is a peripheral or central nervous system cell or progenitors thereof, including, without limitation, embryonic stem cells, neural stem cells, glial cells, astrocytes, neurons and the like, and/or cells in the eye and progenitors thereof, including, but not limited to retinal cells, corneal cells, horizontal cells, and retinal Müller glia. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin, RNA interference molecule and the like.

In one embodiment of the invention, there is provided a method for monitoring or tracking the development or maturation of a cell, the method comprising: 1) introducing into the cell an expression vector comprising an NOV mini-promoter element operably linked to an expressible sequence, wherein the NOV mini-promoter element comprises one or more NOV regulatory elements operably linked in a non-native conformation to an NOV basal promoter element, and wherein the expressible sequence comprises a reporter gene; and 2) detecting the expression of the reporter gene in the cell of in progeny of the cell as a means of determining the lineage, identity or developmental state of the cell or cell progeny. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to one or more of SEQ ID NO: 4-8. In some embodiments, the cell is a peripheral or central nervous system cell or progenitors thereof, including, without limitation, embryonic stem cells, neural stem cells, glial cells, neurons and the like. In some embodiments, the cell is an eye cell or progenitor thereof, including without limitation a retinal cell, a corneal cell, a horizontal cell, a retinal Müller glial cell, and the like.

In certain embodiments of the invention, there is thus provided a method of treatment of a subject having a disease or condition of the brain, the method comprising administering to the subject a therapeutically effective dose of a composition comprising an NOV mini-promoter element, wherein the NOV mini-promoter element comprises one or more NOV regulatory elements operably linked in a non-native conformation to an NOV basal promoter element. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to SEQ ID NO: 4-8. The disease or condition may be chosen from a list including, but not limited to: neuropathies, neurodegenerative disorders, neurodevelopmental disorders, psychiatric disorders, depression, schizophrenia, Alzheimer disease, dementia, and bipolar disorder. The therapeutic or beneficial compound may be any protein of interest, examples include but are not limited to such proteins as a nerve growth factor, an anti-apoptic molecule, an enzyme, and the like. The therapeutic or beneficial compound may be a light-sensitive compound, including, but not limited to, rhodopsin and/or channelrhodopsin.

In certain embodiments of the invention, there is thus provided a method of treatment of a subject having a disease or condition of the eye, the method comprising administering to the subject a therapeutically effective dose of a composition comprising an NOV mini-promoter element, wherein the NOV mini-promoter element comprises one or more NOV regulatory elements operably linked in a non-native conformation to an NOV basal promoter element. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to SEQ ID NO: 4-8. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, including, but not limited to, rhodopsin and/or channelrhodopsin.

SHORT DESCRIPTION OF FIGURES

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIGS. 2A-2D—Ple303 (NOV RRs) expresses in the cortex of the brain and in the horizontal cells of the eye. The Ple303 promoter driving icre expression was constructed and ssAAV9 virus generated (vEMS46). P0 mice were injected intravenously with virions and mice were harvested at P21 and P56 via perfusion and stained overnight for lacZ activity (blue), indicative of promoter activity.

DETAILED DESCRIPTION

The compositions of the present invention include novel polynucleotides comprising NOV promoter elements (also referred to herein as NOV mini-promoters) as well as novel expression vectors comprising said NOV promoter elements (or mini-promoters). The present invention also includes various methods utilizing these novel NOV promoter (or mini-promoter) elements or expression vectors.

The term 'NOV' refers to the gene which encodes the NOV protein, also known as CCN3, encodes a secreted, extracellular matrix (ECM) associated signaling protein. The human homolog of NOV is encoded by the human gene identified as EntrezGene #4856 and is located at chromosomal location 8q24.1. The protein encoded by human NOV has the Protein Accession #CAA65403.1 however other protein accession numbers may also be assigned to this protein. NOV may also include other isoforms and/or splice variants. Other mammalian NOV homologs may include but are not limited to: *Macaca mulatta* (EntrezGene #702196), *Pan troglodytes* (EntrezGene #737818), *Rattus norvegicus* (EntrezGene #81526), *Mus musculus* (EntrezGene #18133).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'NOV basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 3.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'NOV regulatory element', in the context of the present invention and as used herein, is a nucleic acid compound having a sequence with at least 65%, at least 70%, at least 80%, at least 85%, at least 90%, at least 95%, or at least 99% similarity to any one of SEQ ID NO: 4-8. The present invention provides, in certain embodiments as described herein, different promoters of the NOV gene. In some embodiments, the NOV promoter comprises one or more NOV regulatory elements operably linked to a NOV basal promoter.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, or other methods. Other advantages of mini-promoters are apparent to one of skill in the art. In some embodiments of the invention, there are thus provided novel NOV mini-promoters comprising a NOV regulatory element operably linked in a non-native conformation to a NOV basal promoter. In general the spacing between the NOV regulatory element and the NOV basal promoter is not more than about 15 KB, generally not more than about 10 KB, usually not more than about 1 KB, more often not more than about 500 nt, and may be not more than about 100 nt, down to a direct joining of the two sequences. In other embodiments, there is provided a minimal NOV basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, or other methods.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include, but are not limited to, plasmids, cosmids, phage, YAC, BAC, mini-chromosomes, viruses, e.g. retroviruses, adenovirus, lentivirus, SV-40, and the like. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson, Plaehn et al. 1996; Jasin, Moynahan et al. 1996). The HPRT gene has additional advantages as a genomic targeting sequence, for instance its concomitant use as a selectable marker system. Other genomic targeting sequences that may be useful in the present invention are described in the art, for instance (Jasin, Moynahan et al. 1996; van der Weyden, Adams et al. 2002). The genomic targeting signals as described herein are useful in certain embodiments of the present invention.

Introduction of nucleic acids or expression vectors into cells may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

In certain embodiments of the invention, there are provided methods of treatment using the nucleic acids or expression vectors, for instance for gene therapy applications. The nucleic acids or expression vectors of the present invention may be administered in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, intraocular, topical or oral administration. An excipient may include sterile aqueous solutions or dispersions for extemporaneous preparation of sterile injectable solutions or dispersion. Use of such media for preparation of medicaments is known in the art.

The nucleic acids or expression vectors of the present invention may be administered to a subject using a viral delivery system. For instance, the nucleic acids may be inserted into a viral vector using well known recombinant techniques. The subsequent viral vector may then be packaged into a virus, such as adenovirus, lentivirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenously, inhalation, intramuscular, subcutaneous, topical, intraperitoneal, intra-ocular, intra-rectal or intra-vaginal suppository, sublingual, and the like. The compounds of the present invention may be administered as a sterile aqueous solution, or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

NOV Mini-Promoters

The present invention herein provides novel NOV mini-promoter sequences which are capable of effecting transcriptional expression in a spatial and temporal fashion in the brain and/or eye. Certain NOV mini-promoters of the invention comprise minimal NOV promoter elements joined in a non-native configuration, thus providing advantageous characteristics. Also provided are novel expression vector compositions comprising NOV mini-promoters which allow consistent specific spatiotemporal transcription of expression sequences. Also provided are novel methods utilizing these NOV mini-promoters and expression vectors.

The NOV promoters of the invention, as described herein, are referred to as 'mini-promoters' to reflect the fact that the mini-promoters comprise minimal NOV promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance one or more human NOV regulatory elements corresponding to one or more of SEQ ID NO: 4-8, and the human NOV basal promoter element corresponding to SEQ ID NO: 3, or sequences with substantial functional and/or sequence equivalence, is altered. Additionally, the orientation of the different promoter elements may be altered—for instance the regulatory element corresponding to one or more of SEQ ID NO: 4-8 may be inverted relative to the basal promoter element corresponding to SEQ ID NO: 3. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Example, that a human NOV mini-promoter having a sequence corresponding to SEQ ID NO: 2 (also referred to in the Working Example as Ple303), and which is comprised of 4 upstream human NOV regulatory elements (corresponding to SEQ ID NO: 5-8) operably linked in a non-native conformation to a human NOV basal promoter having a nucleic acid sequence corresponding to SEQ ID NO: 3, is capable of directing expression of an expressible sequence which is operably linked downstream of the NOV promoter in specific cell types in different regions of the brain and/or eye. The NOV regulatory elements (SEQ ID NO: 5-8) and NOV basal promoter element (SEQ ID NO: 3) have sequences which are identical to those found in the human NOV gene. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate of an expressible sequence operably linked to a modified promoter sequence that is at least about 75% the transcription rate of the promoter sequence of SEQ ID NO: 1 or 2, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 1 or 2 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

In one embodiment of the invention, there is provided an isolated nucleic acid fragment comprising a NOV mini-promoter, wherein the NOV mini-promoter comprises one or more NOV regulatory elements operably linked in a non-native conformation to a NOV basal promoter. The NOV mini-promoter may have a nucleic acid sequence which is substantially similar in sequence and function to SEQ ID NO: 1 or 2. The NOV basal promoter may have a nucleic acid sequence which is substantially similar in sequence and function to SEQ ID NO: 3. The NOV regulatory element may have a nucleic acid sequence which is substantially similar in sequence and function to one or more of SEQ ID NO: 4-8, e.g. comprising one, two, three, four or five of the provided regulatory elements. The NOV mini-promoters may further be operably linked to an expressible sequence, including, but not limited to, reporter genes, genes encoding a polypeptide of interest, and regulatory RNA sequences such as miRNA, siRNA, and anti-sense RNA. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin, and the like. The expressible sequence may encode an RNA interference molecule.

It is an object of the present invention to provide means of expressing a gene, protein, RNA interference molecule or the like in a cell, tissue or organ. As such, the inventors thus provide novel expression vectors comprising NOV mini-promoters which are capable of accomplishing this task. In one embodiment, there is provided an expression vector comprising a NOV mini-promoter, wherein the NOV mini-promoter comprises one or more NOV regulatory element operably linked in a non-native conformation to an NOV basal promoter. The NOV mini-promoter may have a nucleic acid sequence which is substantially similar in sequence and function to SEQ ID NO: 1 or 2. The NOV basal promoter may have a nucleic acid sequence which is substantially similar in sequence and function to SEQ ID NO: 3. The NOV regulatory element may have a nucleic acid sequence which is substantially similar in sequence and function to one or more of SEQ ID NO: 4-8. The NOV mini-promoter may further be operably linked to an expressible sequence, including, but not limited to, reporter genes, genes encoding a polypeptide of interest, and regulatory RNA sequences such as miRNA, siRNA, and anti-sense RNA. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin, and the like. The expressible sequence may encode an RNA interference molecule. The expression vector may further comprise a genomic targeting sequence. The genomic targeting sequence may be HPRT, e.g. human HPRT, mouse HPRT, and other such HPRT sequences.

The inventors have herein demonstrated that expression vectors comprising novel NOV mini-promoter elements are capable of directing transcription of an expression sequence in specific cell types, for instance in horizontal cells in the retina (eye) or in neuronal cells in the brain. In one embodiment of the invention, there is thus provided a method for expressing a gene, protein, RNA interference molecule or the like in a cell, the method comprising introducing into the cell an expression vector comprising an NOV mini-promoter element, wherein the NOV mini-promoter element comprises one or more NOV regulatory element operably linked in a non-native conformation to a NOV basal promoter element. Cells of interest include cells of the peripheral or central nervous system and progenitors thereof, including, but not limited to, embryonic stem cells, neural stem cells, neurons, glial cells, astrocytes, and microgial cells; and/or cells in the eye and progenitors thereof, including, but not limited to, retinal cells, horizontal cells, corneal cells, and retinal Müller glial cells. The NOV mini-promoter may have a nucleic acid sequence which is substantially similar in sequence and function to SEQ ID NO: 1 or 2. The NOV basal promoter may have a nucleic acid sequence which is substantially similar in sequence and function to SEQ ID NO: 3. The NOV regulatory element may have a nucleic acid sequence which is substantially similar in sequence and function to one or more of SEQ ID NO: 4-8. The NOV mini-promoter may further be operably linked to an expressible sequence, including, but not limited to, reporter genes, genes encoding a polypeptide of interest, and regulatory RNA sequences such as miRNA, siRNA and anti-sense RNA. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising an NOV mini-promoter element, wherein the NOV mini-promoter element comprises one or more NOV regulatory element operably linked in a non-native conformation to a NOV basal promoter element, and wherein the expressible sequence comprises a reporter gene. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to one or more of SEQ ID NO: 4-8. The inventors have demonstrated that expression vectors comprising certain human NOV promoter elements are capable of expression in specific regions of the brain and eye, most notably retinal Muller glial cells in the eye. In some embodiments, the cell is a peripheral or central nervous system cell or progenitors thereof, including, without limitation, embryonic stem cells, neural stem cells, glial cell, neuronal cells, astrocytes, and the like. In some embodiments, the cell is a cell of the eye and progenitors thereof, including without limitation retinal cells, corneal cells, horizontal cells, retinal Müller glial cells, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, channelrhodopsin, RNA interference molecule and the like.

In further embodiments of the invention, there is provided a method for monitoring or tracking the development or maturation of a cell, the method comprising: 1) introducing into the cell a expression vector comprising an NOV mini-promoter element operably linked to an expressible sequence, wherein the NOV mini-promoter element comprises one or more NOV regulatory elements operably linked in a non-native conformation to an NOV basal promoter element, and wherein the expressible sequence comprises a reporter gene; and 2) detecting the expression of the reporter gene in the cell of in progeny of the cell as a means of determining the lineage, identity or developmental state of the cell or cell progeny. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to one or more of SEQ ID NO: 4-8. In such a fashion, one may be able to follow the development of a parent cell as it differentiates into more mature cells. As an example, one could introduce an expression vector comprising the aforementioned NOV mini-promoter elements into a pluripotent stem cell, monitor the expression of the reporter gene that is being expressed by the NOV promoter elements during the maturation and differentiation of the stem cell and thus determine the state of maturation, for instance in the differentiation of the pluripotent stem cell into a specific brain or retinal cell type. The inventors have demonstrated that the NOV mini-promoter elements described herein direct transcriptional expression in certain brain and retinal cell types, and so detection of reporter gene expression in a cell would thus be indicative of the cellular identity of the cell as being a certain type of brain or retinal cell.

The inventors have herein demonstrated that certain NOV mini-promoter elements of the present invention are capable of driving expression in brain, for example the cortex. This surprising expression pattern provides additional methods of use for these mini-promoter elements. For instance, the NOV mini-promoters of the present invention can be utilized in a gene therapy or cell therapy application wherein the NOV mini-promoters are utilized to drive expression of a therapeutic or beneficial compound, such as a protein, in cortical neurons. In such a way, the therapeutic or beneficial compound can be useful for a disease or condition that involves such retinal cells, or which may be improved by expression of the therapeutic or beneficial compound in those cells. In certain embodiments of the invention, there is thus provided a method of treatment of a subject having a disease or condition of the brain, the method comprising administering to the subject a therapeutically effective dose of a composition comprising an NOV mini-promoter element, wherein the NOV mini-promoter element comprises one or more NOV regulatory element operably linked in a non-native conformation to an NOV basal promoter element. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to one or more of SEQ ID NO: 4-8. The disease or condition may be chosen from a list including, but not limited to: neuropathies, neurodegenerative disorders, neurodevelopmental disorders, psychiatric disorders, depression, schizophrenia, Alzheimer disease, dementia, and bipolar disorder. The therapeutic or beneficial compound may be any protein of interest, examples include but are not limited to such proteins as a nerve growth factor, an anti-apoptic molecule, an enzyme, and the like. The therapeutic or beneficial compound may be a light-sensitive compound including, but not limited to, rhodopsin and/or channelrhodopsin.

The inventors have herein demonstrated that certain NOV mini-promoter elements of the present invention are capable of driving expression in retinal horizontal and corneal cells. This surprising expression pattern provides additional methods of use for these mini-promoter elements. For instance, the NOV mini-promoters of the present invention can be utilized in a gene therapy or cell therapy application wherein the NOV mini-promoters are utilized to drive expression of a therapeutic or beneficial compound, such as a protein, in retinal horizontal cells. In such a way, the therapeutic or beneficial compound can be useful for a disease or condition that involves such retinal cells, or which may be improved by expression of the therapeutic or beneficial compound in those cells. In certain embodiments of the invention, there is thus provided a method of treatment of a subject having a disease or condition of the eye, the method comprising administering to the subject a therapeutically effective dose of a composition comprising an NOV mini-promoter element, wherein the NOV mini-promoter element comprises one or more NOV regulatory element operably linked in a non-native conformation to an NOV basal promoter element. The NOV mini-promoter element may have a nucleic acid sequence substantially similar in sequence and function to SEQ ID NO: 1 or 2. The NOV basal promoter element may have a nucleic acid sequence substantially similar in sequence and function to SEQ ID NO: 3. The NOV regulatory element may have a nucleic acid sequence substantially similar in sequence and function to one or more of SEQ ID NO: 4-8. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, including, but not limited to: rhodopsin, and/or channelrhodopsin.

The inventors herein further describe the present invention by way of the following non-limiting examples:

WORKING EXAMPLES

General Methods
Virus Generation and Analysis
Virus Production

The Ple263 and Ple303 (NOV) MiniPromoters were generated by direct synthesis by DNA2.0 (Menlo Park, Calif., USA) and by Integrated DNA Technologies (Coralville, Iowa, USA) respectively (SEQ ID NO: 1 or 2), resulting in plasmids pEMS1940 and pEM1962. Promoter elements were cloned into the pEMS1980 backbone, containing the iCre reporter, using AvrII and AscI restriction enzymes, generating plasmid pEMS2025 for Ple303. One μg of plasmid containing either the Ple303 MiniPromoter was prepared by miniprep and sent to the Vector Core at the University of Pennsylvania (Philadelphia, Pa., USA) to be made into AAV9 serotype virus.

Virus Injection

B6-Gt(ROSA26)$^{tm1Sor}$ females were crossed to 129-Gt (ROSA26)$^{tm1Sor}$ to yield hybrid F1 homozygous pups for injecting virus. Plug checks were performed on the females such that the day of birth could be accurately estimated. P0 pups were used for virus injections. If the female gave birth in the morning, virus was injected in the afternoon. If she gave birth in the afternoon, virus was injected the next morning. A standard injection into the superficial temporal vein of a newborn pup was performed using $1 \times 10^{13}$ GC/mL (genome copies per milliliter) virus in a total volume of 50 μL (in PBS) with a 30 gauge needle and a 1 cc syringe. After injections, pups were tattooed for identification and returned to their cage.

Harvesting of Animals

Virus-injected mice were harvested at P21 or P56 (post-natal day 21 or 56). Animals were given a lethal dose of avertin injected intraperitoneally. Thereafter perfusion with 1×PBS for 2 minutes and 4% PFA/PBS for 8 minutes was performed. Tissues were harvested and post-fixed for 1 hour at 4° C. The tissues were then stored in 0.02% Azide/PBS at 4° C.

Histology

Tissues were cryoprotected in 30% sucrose/PBS overnight at 4° C. After embedment in OCT the following day, 20 μm sections were directly mounted onto slides. For X-gal staining, tissues were rinsed in PBS and Triton-X/PBS and stained in 0.1% X-gal solution overnight at 30-35° C. After staining sections were rinsed and counterstained with neutral red, dehydrated and mounted with coverslips. For co-labeling of X-gal with markers using immunohistochemistry, standard IHC procedure was followed and the X-gal stain was performed either prior to primary antibody incubation or between primary and secondary antibodies, depending on the strength of the X-gal stain. X-gal stains blue any cells that have recombined the Gt(ROSA26)$^{tm1Sor}$ locus due to iCre recombinase activity and thus expressing the β-galactosidase protein.

Example 1

Selection of NOV Mini-promoter Elements

The Ple263 construct was designed based on the NOV gene. It combines a basal promoter (SEQ ID NO: 3) along with five upstream conserved elements with putative regulatory function segment 1 (SEQ ID NO: 4), segment 2 (SEQ ID NO: 5), segment 3 (SEQ ID NO: 6), segment 4 (SEQ ID NO: 7), and segment 5 (SEQ ID NO: 8). These elements were generated by de novo DNA synthesis and the construct matches the human genome sequence (hg19, February 2009). The Ple303 construct was designed based on the NOV gene. The construct includes a basal promoter (SEQ ID NO: 3) along with four upstream conserved elements with putative regulatory function segment 1 (SEQ ID NO: 5), segment 2 (SEQ ID NO: 6), segment 3 (SEQ ID NO: 7) and segment 4 (SEQ ID NO: 8). These elements were generated by de novo DNA synthesis and the construct matches the human genome sequence (hg19, February 2009).

Example 2

Expression of Reporter in Brain and Eye by Ple303 Mini-Promoter

The Ple303 construct was subsequently tested in ssAAV9 (recombinant single-stranded adeno-associated virus) driving the icre (improved cre recombinase) reporter, resulting in vEMS46. Mice were injected intravenously with virus at post-natal day 0 (P0) (method of (Foust et al. 2009)), and expression analyzed at P21 and P56 via recombination of the reporter locus Gt(ROSA26)SortmSor1 (Soriano 1999). Once recombined, this locus expresses the β-galactosidase (lacZ gene) enzyme. Mice were harvested by cardiac perfusion, sectioned, and stained with the X-gal substrate, which leaves a blue product after enzymatic cleavage by beta-galactosidase.

Figure 1:
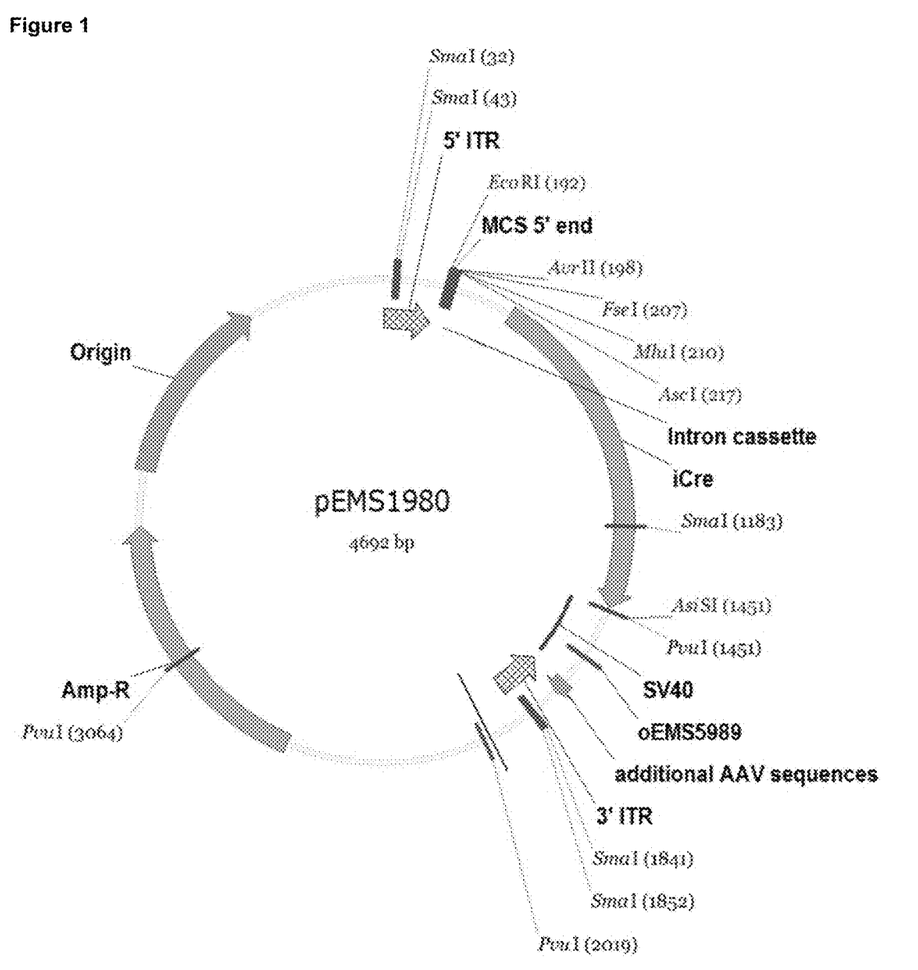
FIG. 1—DNA expression vector (pEMS1980) into which NOV promoter elements were inserted for expression studies. The NOV promoter with a nucleic acid sequence corresponding to SEQ ID NO: 1 or 2 was inserted into the multiple cloning site (MCS) of the pEMS1980 vector such that it became operably linked to the icre recombinase gene. The final construct, called Ple263 (containing SEQ ID NO: 1) or Ple303 (containing SEQ ID NO: 2), also contained an ampicillin resistance gene (AmpR) for screening, and a transcriptional termination sequence (SV40 polyA), as well as other elements necessary for vector replication and gene expression.
Figure 2A:
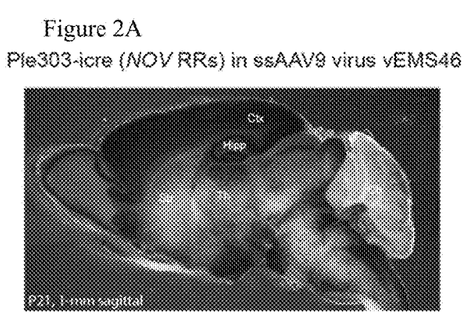
FIG. 2A, a cryosection of the P21 brain demonstrates expression throughout many brain regions, but with reduced expression in the striatum, thalamus and cerebellum.
Figure 2B:
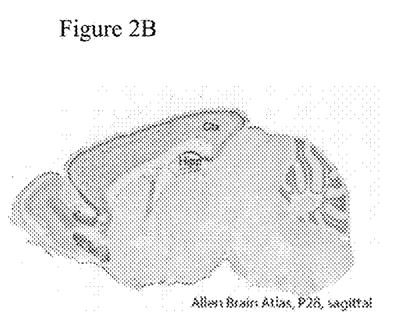
FIG. 2B, a matched sagittal image from the Allen Brain Atlas shows similar strong cortical and hippocampal CA1 staining for endogenous Nov as detected by in situ hybridization (Lein et al. 2007; Ng et al. 2009).
Figure 2C:
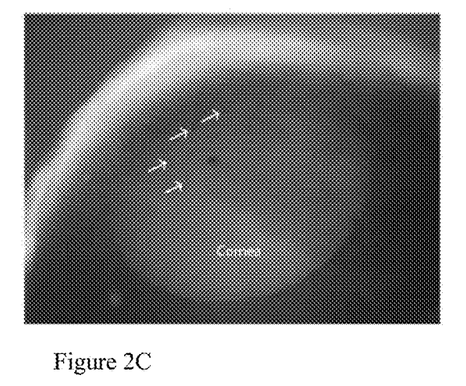
FIG. 2C, in the cornea patches of blue staining for lacZ are observed (white arrows).
Figure 2D:
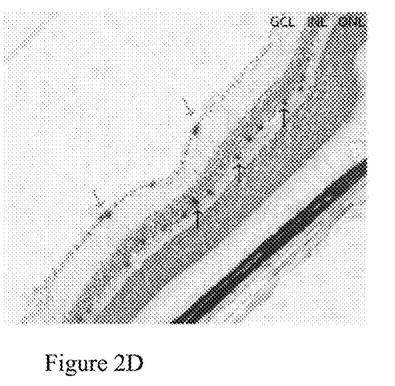
FIG. 2D, in the retina, there was staining of cells in the GCL (grey arrows), as well as in the outermost INL (black arrows); the latter is representative of horizontal cells. Cb, cerebellum; Ctx, cortex; GCL, ganglion cell layer; Hipp, hippocampus; INL, inner nuclear layer; ONL, outer nuclear layer; P, post-natal day; RR, regulatory regions; Str, striatum; Th, thalamus.

In the brain, Ple303-driven icre expression resulting in recombination of the ROSA26 locus, was detected via lacZ immunohistochemistry throughout many brain regions. In particular, the majority of cortical cells are stained (FIG. 1A), similar to that observed in the adult mouse brain by in situ hybridization performed by the Allen Brain Institute (FIG. 1B). In the Allen Brain Atlas (ABA), extensive labeling in the superficial, midlevel and deep cortex, piriform cortex and hippocampal CA1 and in the basal and lateral nuclei of amygdala. In select sagittal sections, the continuum between hippocampal CA1 region into amygdaloid-hippocampal region and posteromedial cortical amygdala is shown, and olfactory nuclei/bulb. Endogenous NOV expression has been observed in the adult rat cerebral cortex and amygdala (Su et al. 2001). Although some expression was observed in the Purkinje cells in the cerebellum (FIG. 1A), the human-sequence-based Ple303 staining is much weaker and more rare than in situ hybridization in rat would suggest (Le Dréau et al. 2010; Su et al. 2001). However, more similar to our Ple303 data is that of the ABA mouse images, which only show weak in situ hybridization staining in Purkinje cells in some sections.

The cornea of the Ple303 mouse eye showed punctate blue staining, indicative of activity in corneal cells (FIG. 1C, white arrows). In the retina, staining in the horizontal cells was observed (FIG. 1D, black arrows). Although additional staining was observed in the inner nuclear and ganglion cell layers (FIG. 1D, grey arrows), background staining observed in the virus-delivered icre system does not allow any conclusions to be drawn about this aspect of expression. CCN3 is known to be expressed in the horizontal cells of the retina (Laurent et al. 2013). In addition, expression of Nov/Ccn3 has been reported in Müller glia (Laurent et al. 2013). No staining indicative of Müller glia was observed in this system.

LIST OF SEQUENCES

SEQ ID NO: 1; Ple263 human NOV mini-promoter element
SEQ ID NO: 2; Ple303 human NOV mini-promoter element
SEQ ID NO: 3; NOV Basal Promoter element
SEQ ID NO: 4; NOV Regulatory Element #1
SEQ ID NO: 5; NOV Regulatory Element #2
SEQ ID NO: 6; NOV Regulatory Element #3
SEQ ID NO: 7; NOV Regulatory Element #4
SEQ ID NO: 8; NOV Regulatory Element #5

What is claimed is:

1. An isolated polynucleotide comprising a NOV mini-promoter wherein the NOV mini-promoter comprises at least one NOV regulatory element with at least 95% sequence identity to SEQ ID NO: 4, 5, 6, 7, or 8; operably joined to a NOV basal promoter with at least 95% sequence identity to SEQ ID NO: 3 wherein the spacing between the NOV regulatory element and the NOV basal promoter is not more than 500 nucleotides (nt).

2. The polynucleotide of claim 1, comprising a NOV mini-promoter with at least 95% sequence identity to SEQ ID NO: 1.

3. The polynucleotide of claim 1, comprising a NOV mini-promoter with at least 95% sequence identity to SEQ ID NO: 2.

4. The isolated polynucleotide of claim 1, operably linked to an expressible sequence.

5. A vector comprising the isolated polynucleotide of claim 1.

6. An isolated cell comprising the vector of claim 5.

7. The cell of claim 6, wherein the vector is stably integrated into the genome of the cell.

8. The cell of claim 6, wherein the cell is a stem cell, a retinal cell or a brain cell.

9. A method of expressing a sequence of interest, the method comprising operably linking the sequence of interest to the polynucleotide of claim 1; and introducing into a cell permissive for expression from the NOV mini-promoter.

10. The method of claim 9, wherein the cell is a retinal cell or a progenitor thereof.

11. The method of claim 9, wherein the cell is a brain cell or a progenitor thereof.

12. An isolated polynucleotide comprising a NOV mini-promoter wherein the NOV mini-promoter comprises at least one NOV regulatory element with at least 99% sequence identity to SEQ ID NO: 4, 5, 6, 7, or 8 operably joined to an NOV basal promoter with at least 99% sequence identity to SEQ ID NO: 3, wherein the spacing between the NOV regulatory element and the NOV basal promoter is not more than 500 nucleotides (nt).

13. The polynucleotide of claim 12 wherein the NOV mini-promoter has at least 99% sequence identity to SEQ ID NO: 1.

14. The polynucleotide of claim 12 wherein the NOV mini-promoter has at least 99% sequence identity to SEQ ID NO: 2.

15. The isolated polynucleotide of claim 12, operably linked to an expressible sequence.

* * * * *